United States Patent
Richard et al.

(10) Patent No.: US 10,246,702 B1
(45) Date of Patent: Apr. 2, 2019

(54) COMPOSITIONS AND METHODS FOR LABELING TARGET NUCLEIC ACID MOLECULES

(71) Applicants: Cynthia L. Richard, Essex, MA (US); Brendan Galvin, Ipswich, MA (US)

(72) Inventors: Cynthia L. Richard, Essex, MA (US); Brendan Galvin, Ipswich, MA (US)

(73) Assignee: New England Biolabs, Inc., Ipswich, MA (US)

(*) Notice: Subject to any disclaimer, the term of this patent is extended or adjusted under 35 U.S.C. 154(b) by 371 days.

(21) Appl. No.: 15/051,064

(22) Filed: Feb. 23, 2016

Related U.S. Application Data

(60) Provisional application No. 62/142,104, filed on Apr. 2, 2015, provisional application No. 62/119,643, filed on Feb. 23, 2015.

(51) Int. Cl.
- *C12N 15/10* (2006.01)
- *C12Q 1/68* (2018.01)
- *C12Q 1/6806* (2018.01)

(52) U.S. Cl.
CPC ....... *C12N 15/1065* (2013.01); *C12Q 1/6806* (2013.01)

(58) Field of Classification Search
None
See application file for complete search history.

(56) References Cited

U.S. PATENT DOCUMENTS

| | | |
|---|---|---|
| 5,635,400 A | 6/1997 | Brenner |
| 8,288,097 B2 | 10/2012 | Mikawa |
| 2012/0156729 A1* | 6/2012 | Sooknanan ........ C12N 15/1096 435/91.2 |
| 2014/0287468 A1 | 9/2014 | Richard |
| 2015/0119261 A1 | 4/2015 | Richard |

FOREIGN PATENT DOCUMENTS

| | | |
|---|---|---|
| EP | 0799897 | 10/1997 |

OTHER PUBLICATIONS

Casbon, et al., A Method for counting PCR template molecules with application to next-generation sequencing, Nuc. Acids Res., 12, e81 (2011).
Brenner, et al., Proc. Natl. Acad. Sci., 97: 1665-1670 (2000).
Newman, et al., An ultrasensitive method for quantitative circulating tumor DNA with broad patient coverage, Nat. Med. 20: 548-54 (2014).
Shendure, et al., Next-generation DNA sequencing, Nature, 26:1135-1145 (2008).
Mardis, The impact of next-generation sequencing technology on genetics, Trends in Genetics, 24:133-141 (2007).
Su, et al., Next-generation sequencing and its applications in molecular diagnostics, Expert Rev Mol Diagn, 11(3):333-343, 2011.
Zhang, et al., The impact of next-generation sequencing on genomics, Journal of Genetics and Genomics 38:95-109 (2011).

* cited by examiner

*Primary Examiner* — Karen S. Weiler
(74) *Attorney, Agent, or Firm* — New England Biolabs, Inc; Harriet M. Strimpel

(57) ABSTRACT

Provided herein are methods and compositions for labeling target nucleic acid molecules with molecular barcodes.

9 Claims, 6 Drawing Sheets

Specification includes a Sequence Listing.

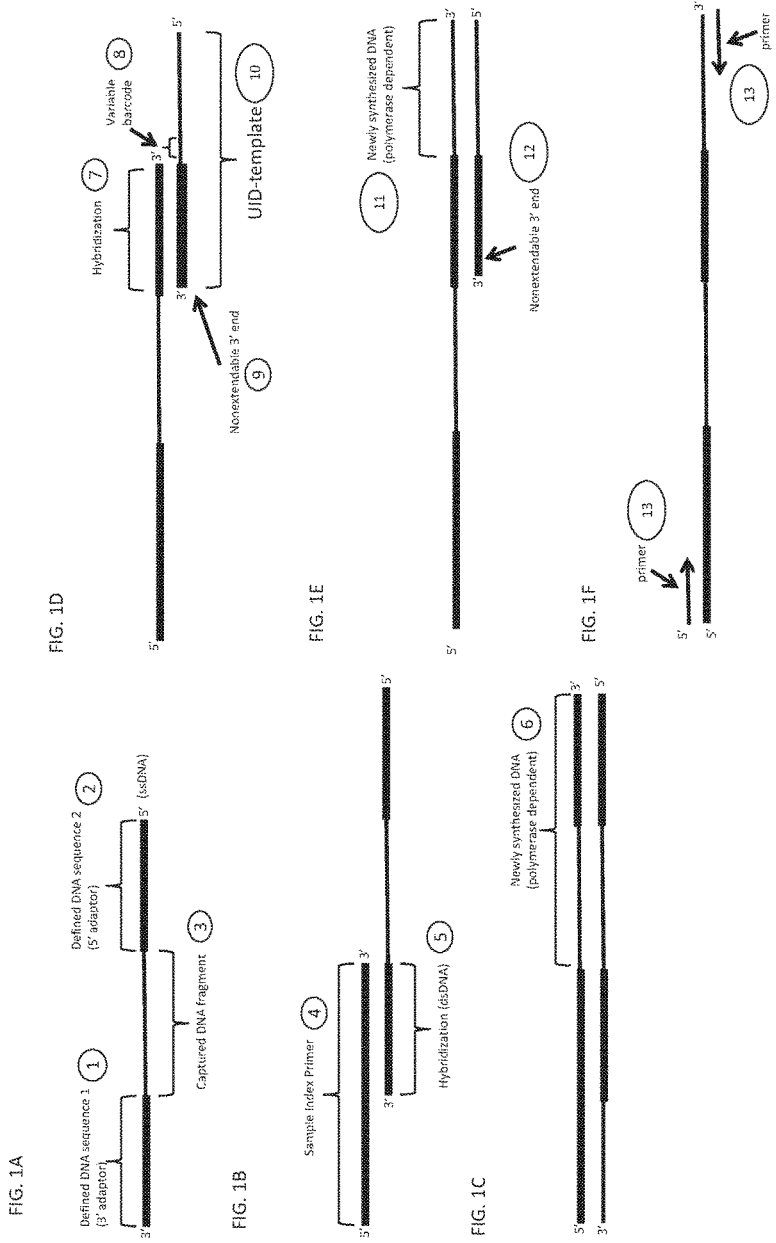

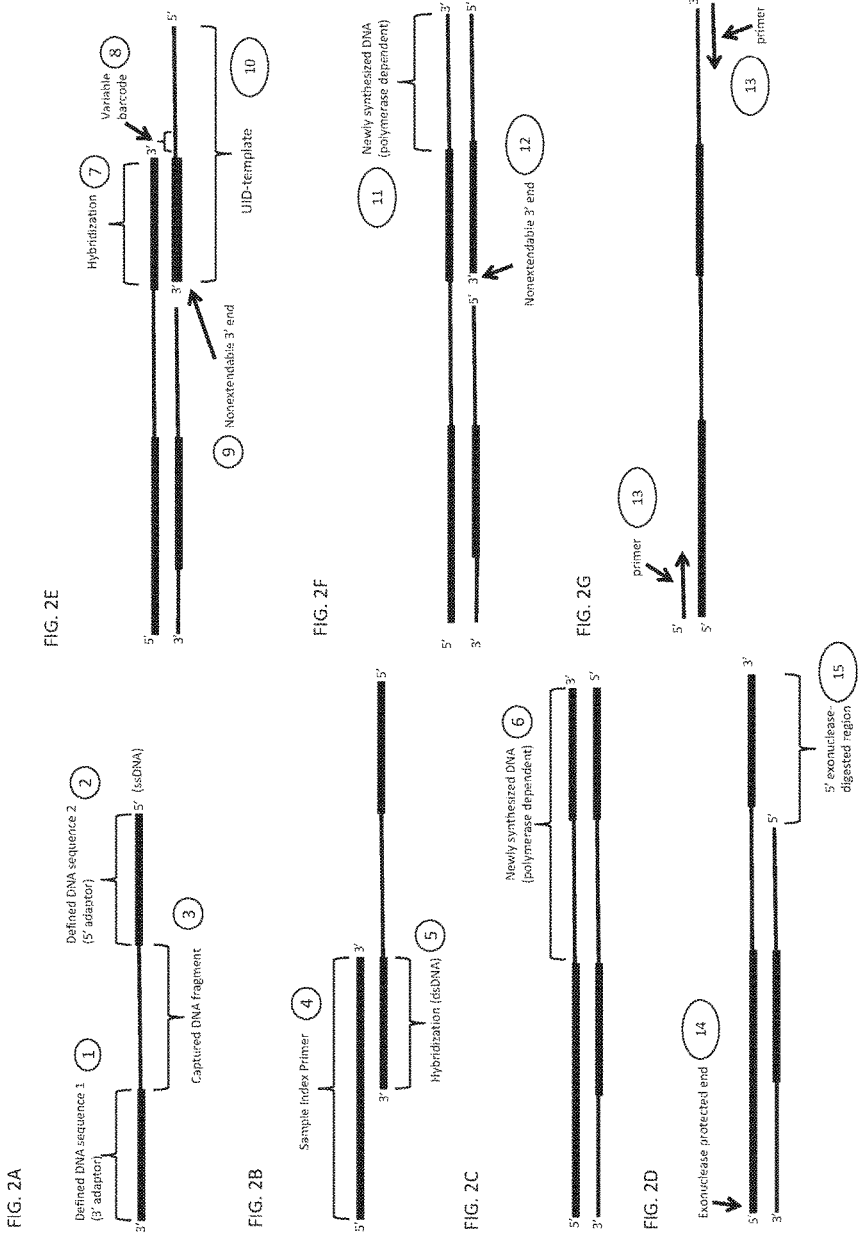

FIG. 3A (SEQ ID NO: 1)
5'-CTGACCTCAAGTCTCCACAGCGAATTGTTGACTGTGACTGGAGTTCAGACGTGTGCTCTTCCGATCT-captured library-TCTAGCCTTCTCGCAGCACATCCCTTTCTCACA-5'-p
3'-CTGACCTCAAGTCTGCACGAGAAGGCTAG-captured library-TCTAGCCTTCTCCAGCAGCAACATCCCTTTCTCACA-5'-p
                                                                                              (SEQ ID NO: 2)
Read 2 sequencing primer                                                 Read 1 sequencing primer

FIG. 3B p7                              index
5'-C-s-A-s-A-s-G-s-C-s-A-s-GAAGACGGCCATACGAGATTGTTGACTGTGACTGGAGTTCAGACGTGTGCTCTTCCGATCT-3' (SEQ ID NO: 3)
                                                     3'-CTGACCTCAAGTCTGCACACGAGAAGGCTAG-A(captured library)-TCTAGCCTTCTCCAGCACATCCCTTTCTCACA-5'-p
                                                                                                                                        (SEQ ID NO: 2)

FIG. 3C (SEQ ID NO: 3)
5'-C-s-A-s-A-s-G-s-C-s-A-s-GAAGACGGCCATACGAGATTGTTGACTGTGACTGGAGTTCAGACGTGTGCTCTTCCGATCT-copy of capture--AGATCGGAAGAGCGTCGTGTAGGGAAAGAGTGT-3'
                                                                                                                            (SEQ ID NO: 4)
                                                     3'-CTGACCTCAAGTCTGCACACGAGAAGGCTAG-A(captured library)-TCTAGCCTTCTCCAGCACATCCCTTTCTCACA-5'-p
                                                                                                                                        (SEQ ID NO: 2)

FIG. 3D (SEQ ID NO: 3)
5'-C-s-A-s-A-s-G-s-C-s-A-s-GAAGACGGCCATACGAGATTCTTGACTGTGACTGGAGTTCAGACGTGTGCTCTTCCGATCT-copy of capture--AGATCGGAAGAGCGTCGTGTAGGGAAAGAGTGT-3'
                                                                                                                            (SEQ ID NO: 4)
                                                     3'-CTGACCTCAAGTCTGCACGAGAAGGCTAG-A(captured library)-5' (SEQ ID NO: 1)

FIG. 3E

5'-...copy of capture--AGATCGGAAGAGCGTCGTGTAGGGAAAGAGTGT-3' (SEQ ID NO: 4)
3AmMo-3'-TTCTCGCAGCACATCCCTTTCTCACANNNNNNNNCACATCTAGAGCCACCACGCGGCATAGTAA-5'
                                                 barcode                    P5
            (SEQ ID NO: 5)

FIG. 3F

5'...copy of capture---AGATCGGAAGAGCGTCGTGTAGGGAAAGAGTGTNNNNNNNNGTGTAGATCGGTGGTCGCCCTATCATT-3'
(SEQ ID NO: 6)
3'AmMO-3'-TTCTCGCAGCCACATCCCTTTCTCACANNNNNNNNCACATCTAGAGCCACCAGCGGCATAGTAA-5'
(SEQ ID NO: 5)

FIG. 3G

5'...copy of capture---AGATCGGAAGAGCGTCGTGTAGGGAAAGAGTGTNNNNNNNNGTAGATCGGTGGTCGCCCTATCATT-3'
(SEQ ID NO: 6)
3'-AGAGCCACCAGCGGCATAGTAA-5'
PCR1
(SEQ ID NO: 8)

(SEQ ID NO: 7)
PCR2
3'-GTTCGTTCTGCCGTATGCTC-3'
5'-CAAGCAGAAGACGGCATACGAGATTGTGACTGGAGTTCAGACGTGTGCTCTTCCGATCT-copy of capture---AGATCGGAAGAGCGTCGTGTAGGGAAAGAGTGTNNNNNNNNGTAGATCGGTGGTCGCCCTATCATT-3'
(SEQ ID NO: 3)

SEQUENCE LISTING

```
<160> NUMBER OF SEQ ID NOS: 8

<210> SEQ ID NO 1
<211> LENGTH: 31
<212> TYPE: DNA
<213> ORGANISM: Artificial Sequence
<220> FEATURE:
<223> OTHER INFORMATION: Synthetic construct

<400> SEQUENCE: 1
ctgacctcaa gtctgcacac gagaaggcta g                              31

<210> SEQ ID NO 2
<211> LENGTH: 33
<212> TYPE: DNA
<213> ORGANISM: Artificial Sequence
<220> FEATURE:
<223> OTHER INFORMATION: Synthetic construct

<400> SEQUENCE: 2
tctagccttc tcgcagcaca tccctttctc aca                            33

<210> SEQ ID NO 3
<211> LENGTH: 60
<212> TYPE: DNA
<213> ORGANISM: Artificial Sequence
<220> FEATURE:
<223> OTHER INFORMATION: Synthetic construct

<400> SEQUENCE: 3
gaagacggca tacgagattg ttgactgtga ctggagttca gacgtgtgct cttccgatct    60
```

```
<210> SEQ ID NO 4
<211> LENGTH: 33
<212> TYPE: DNA
<213> ORGANISM: Artificial Sequence
<220> FEATURE:
<223> OTHER INFORMATION: Synthetic construct

<400> SEQUENCE: 4
agatcggaag agcgtcgtgt agggaaagag tgt                           33

<210> SEQ ID NO 5
<211> LENGTH: 63
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (27)..(34)
<223> OTHER INFORMATION: n is a, c, g, or t

<400> SEQUENCE: 5
ttctcgcagc acatcccttt ctcacannnn nnnncacatc tagagccacc agcggcatag    60
taa                                                                  63

<210> SEQ ID NO 6
<211> LENGTH: 70
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (34)..(41)
<223> OTHER INFORMATION: n is a, c, g, or t

<400> SEQUENCE: 6
agatcggaag agcgtcgtgt agggaaagag tgtnnnnnnn ngtgtagatc tcggtggtcg    60
ccgtatcatt                                                           70

<210> SEQ ID NO 7
<211> LENGTH: 22
<212> TYPE: DNA
<213> ORGANISM: Artificial Sequence
<220> FEATURE:
<223> OTHER INFORMATION: Synthetic construct

<400> SEQUENCE: 7
gttcgtcttc tgccgtatgc tc                                            22

<210> SEQ ID NO 8
<211> LENGTH: 22
<212> TYPE: DNA
<213> ORGANISM: Artificial Sequence
<220> FEATURE:
<223> OTHER INFORMATION: Synthetic construct

<400> SEQUENCE: 8
agagccacca gcggcatagt aa                                            22
```

COMPOSITIONS AND METHODS FOR LABELING TARGET NUCLEIC ACID MOLECULES

BACKGROUND

Next generation sequencing (NGS) has the potential to be an invaluable tool for the diagnosis and treatment of many different diseases and disorders. To reduce the cost of sequencing and the burden of data analysis, a target enrichment process can be used to increase the relative abundance of target sequences in a nucleic acid library prior to performance of the NGS reaction (e.g., as described US 2014/0287468, which is hereby incorporated by reference in its entirety).

Compatibility between target enrichment methods and multiplex sequencing processes is critical because the reduced complexity of enriched target libraries requires multiplex sequencing to be cost effective. Nearly all multiplex sequencing approaches include the labeling of individual libraries with a library-specific nucleic acid barcode, referred to as a "multiplex identifier nucleotide sequence," or "MID," through the addition of a MID to a platform-specific adapter sequence or a PCR primer. Because the sequence of the MID corresponds to the originating library, multiple libraries incorporating distinct MIDs can be combined and sequenced in a single sequencing reaction and, following sequencing, the MIDs can be used in silico to associate each resulting sequence with the library from which it originated.

In addition to MIDs, some target enrichment protocols also label individual DNA molecules with molecule-specific nucleic acid barcodes, referred to as "unique identifier sequences," or "UIDs," such as a degenerate base region (DBR), prior to amplification. The presence of such sequences makes it possible to distinguish unique DNA molecules from PCR duplicates, enabling the more accurate identification and quantification of unique DNA molecules and mutations.

As the diagnostic power of genome and transcriptome analysis increases, improved methods and compositions for the labeling of nucleic acid libraries with library-specific sequences and/or molecule-specific sequences are desirable to facilitate the use of target enrichment methods with multiplex NGS processes.

SUMMARY

Provided herein are methods and compositions for labeling target nucleic acid molecules with molecular barcodes (e.g., with sample-specific barcodes and/or with molecule-specific barcodes). Certain embodiments of the methods and compositions provided herein can be useful, for example, to facilitate the performance of multiplex NGS processes on target-enriched polynucleotide libraries and/or for enabling accurate identification and quantification of unique polynucleotides molecules in a polynucleotide library.

In certain aspects, provided herein is a method of barcode labeling a library of polynucleotide molecules. The barcodes can be sample-specific barcodes (i.e., multiplex identifier sequences, or MIDs) and/or with molecule-specific barcodes (i.e., UIDs).

In certain aspects, provided herein is a method of barcode labeling a library of polynucleotide molecules that include for example, a 3' adapter, a genomic DNA, cDNA or RNA sequence and a 5' adapter. In certain embodiments, the method includes a step of contacting the library of polynucleotide molecules with primers (e.g., sample index primers) comprising a first hybridization sequence (i.e., a sequence capable of hybridizing to at least a portion of the 3' adapter) and, optionally also comprising a sample-specific barcode sequence located 5' of the first hybridization sequence, wherein the primers are contacted with the polynucleotide library under conditions such that the first hybridization sequence hybridizes to a region of the 3' adapter of the library of polynucleotide molecules. In some embodiments, the method comprises incubating the hybridized polynucleotide molecules with a polymerase such that the polymerase extends 3' end of the primers (e.g., sample index primers) to form primer extension products comprising, in 5' to 3' order, a known sequence, (optionally) a sample-specific barcode sequence, a sequence complementary to at least a portion of the 3' adapter, a sequence complementary to the genomic DNA, cDNA or RNA derived sequence, and a sequence complementary to the 5' adapter. In some embodiments, the method includes contacting the primer extension products with UID-template oligonucleotides comprising, in 3' to 5' order, a non-extendable 3' end, a second hybridization sequence (i.e., a sequence capable of hybridizing to at least a portion of the sequence complementary to the 5' adapter), and a variable barcode sequence under conditions such that the second hybridization sequence hybridizes to a 3' terminal region of the sequence complementary to the 5' adapter. In some embodiments, the method includes incubating the hybridized primer extension products with a polymerase such the polymerase extends the 3' end of the primer extension products to form a further extended primer extension product comprising, in 5' to 3' order, a known sequence, (optionally) the sample-specific barcode sequence, the sequence complementary to at least a portion of the first adapter, the sequence complementary to the genomic DNA, cDNA or RNA derived sequence, the sequence complementary to the second adapter, and a sequence complementary to the variable barcode sequence of the oligonucleotide. In some embodiments, the method includes amplifying the further extended primer extension products formed in step (e.g., using PCR or other amplification method known in the art). In some embodiments, the method includes the step of denaturing the primer extension products from the polynucleotide molecules before contacting the primer extension products with the UID-template oligonucleotides. In some embodiments, the 5' terminus of the sample index primer is protected from exonuclease digestion and the method further comprises the step of incubating the primer extension product/polynucleotide library molecule complex with a 5' exonuclease such that a 5' terminal sequence is removed from the polynucleotide molecules of the library before contacting the primer extension products with the UID-template oligonucleotides. In some embodiments, the method further comprises the step of performing a sequencing process (e.g., a NGS process) on the amplification products.

In certain aspects, provided herein is a method of barcode labeling primer extension products formed from a library of polynucleotide molecules. In some embodiments, the method includes contacting primer extension products with UID-template oligonucleotides, wherein: (i) the primer extension products are formed from a library of polynucleotide molecules; (ii) the primer extension products comprise, in 5' to 3' order, a sequence complementary to at least a portion of a first adapter, a sequence complementary to a genomic DNA, cDNA. or RNA derived sequence, and a sequence complementary to a second adapter; (iii) the oligonucleotides comprise, in 3' to 5' order, a non-extendable 3' end, a hybridization sequence (i.e., a sequence capable of hybridizing to at least a portion of the sequence complementary to the 5' adapter), and a variable barcode sequence; and (iv) the primer extension products are contacted with the UID-template oligonucleotides such that the hybridization sequence hybridizes to a 3' terminal region of the sequence complementary to the second adapter. In some embodiments the method includes the step of incubating the hybridized primer extension products with a polymerase such the polymerase extends the 3' end of the primer extension products to form a further extended primer extension product comprising, in 5' to 3' order, the sequence complementary to at least a portion of the first adapter, the sequence complementary to the genomic DNA, cDNA or RNA derived sequence, the sequence complementary to the second adapter, a sequence complementary to the variable barcode sequence of the UID-template oligonucleotides, and additional known sequence. In certain embodiments, the method includes amplifying the further extended primer extension products (e.g., using PCR). In some embodiments, the method further comprises the steps of contacting the library of polynucleotide molecules with primers comprising a 3' adapter hybridization sequence such that the 3' adapter hybridization sequence hybridizes to a region of the 3' adapter; and incubating the resulting hybridized DNA molecules with a polymerase such that the polymerase extends 3' end of the primers to form the primer extension products. In some embodiments, the method includes the step of denaturing the primer extension products from the DNA molecules before contacting the primer extension products with the UID-template oligonucleotides. In some embodiments, the 5' terminus of the sample index primer is protected from exonuclease digestion and the method further comprises the step of incubating the primer extension product/polynucleotide library molecule complex with a 5' exonuclease such that a 5' terminal sequence is removed from the DNA molecules of the library before contacting the primer extension products with the UID-template oligonucleotides. In some embodiments, the method further comprises the step of performing a sequencing process (e.g., a NGS process) on the amplification products.

In certain aspects, provided herein is a method of barcode labeling a library of polynucleotide molecules comprising, in 3' to 5' order, a first adapter, a sequence derived from genomic DNA, cDNA or RNA, and a second adapter comprising an unreplicable region using a terminal transferase. In certain embodiments, the method includes contacting the library of polynucleotide molecules with primers comprising a first adapter hybridization sequence such that the first adapter hybridization sequence hybridizes to a region of the first adapter. In some embodiments, the method includes incubating the hybridized polynucleotide molecules with a polymerase such that the polymerase extends 3' end of the primers to form primer extension products comprising, in 5' to 3' order, a sequence complementary to at least a portion of the first adapter, a sequence complementary to the genomic DNA, cDNA, or RNA derived sequence, and a sequence complementary to the portion of the second adapter that is 3' of the unreplicable region. In some embodiments, the method includes incubating the products of the primer extension reaction with a 3' terminal transferase such that a random nucleic acid sequence is added to the 3' terminus of the primer extension products. In some embodiments, the method includes incubating the products of the terminal transferase reaction with a polymerase such that the polymerase further extends the primer extension products to form a further extended primer extension product comprising, in 5' to 3' order, the sequence complementary to at least a portion of the first adapter, the sequence complementary to the genomic DNA, cDNA or RNA derived sequence, the sequence complementary to the portion of the second adapter that is 3' of the unreplicable region, the random nucleic acid sequence, and a sequence complementary to a portion of the second adapter that is 5' of the unreplicable region. In some embodiments, the method further comprises the step of amplifying the further extended primer extension product. In some embodiments, the method further comprises the step of performing a sequencing process (e.g., a NGS process) on the product of the amplification reaction.

In certain aspects, provided herein is a method of barcode labeling a library of polynucleotide molecules comprising a 3' adapter, a sequence derived from genomic DNA, cDNA or RNA, and, optionally, a 5' adapter using a terminal transferase. In some embodiments, the method includes contacting the library of polynucleotide molecules with primers comprising a 3' adapter hybridization sequence such that the 3' adapter hybridization sequence hybridizes to a region of the 3' adapter. In some embodiments, the method includes incubating the hybridized DNA molecules with a polymerase such that the polymerase extends 3' end of the sample index primers to form primer extension products. In some embodiments, the method includes incubating the primer extension products with a 3' terminal transferase such that a random nucleic acid sequence is added to the 3' terminus of the primer extension products. In some embodiments, a single stranded (ss) adapter is ligated to the 3' end of the random nucleic acid sequence. In some embodiments, a double stranded (ds) adapter is ligated to the 3' end of the random nucleic acid sequence wherein the adapter comprises a sequence complementary to the nucleic acid sequence on the primer extension product. In some embodiments, the method further comprises amplifying the product of the ligation reaction. In some embodiments, the method further comprises the step of performing a sequencing process (e.g., a NGS process) on the product of the amplification reaction.

In any of the above embodiments, the method may further comprise removing a 5' terminal sequence from the polynucleotide molecules of the library after the initial extension step and prior to the next extension step, to leave a 3' overhang. In these embodiments the 5' terminus of the sample index primer may be protected from exonuclease digestion and the 5' terminal sequence of the polynucleotide molecules of the library may be removed by an exonuclease. Alternatively, the second adapter may comprise one or more deoxyuridines, and the 5' terminal sequence of the polynucleotide molecules of the library may be removed using uracil DNA glycosylase (UDG) and the DNA endonuclease VIII, e.g., using USER™ (New England Biolabs, Ipswich, Mass.).

In certain aspects, provided herein is a composition useful in the performance of the methods described herein. In some embodiments, the composition comprises: (a) a mixture of primer extension products formed from a library of polynucleotide molecules comprising, in 3' to 5' order, a first adapter, a sequence derived from genomic DNA, cDNA or RNA, and a second adapter wherein the primer extension products comprise, in 5' to 3' order, a sequence complementary to the first adapter, a sequence complementary to the genomic DNA, cDNA or RNA derived sequence; and the sequence complementary to the second adapter; and (b) an excess amount of a oligonucleotides wherein the oligonucleotides comprise, in 3' to 5' order, a non-extendable 3' end, a sequence capable of hybridizing to the 3' terminal region of the primer extension products and a variable barcode sequence. In some embodiments, the molar ratio of primer extension product to synthetic oligonucleotide is between 1:1 and 1:1×10$^{12}$. For example, in some embodiments, the molar ratio of primer extension product to synthetic oligonucleotide is at least 1:1, 1:10, 1:50, 1:100, 1:500, 1:1000, 1:1×10$^4$, 1:1×10$^5$, 1:1×10$^6$, 1:1×10$^7$, 1:1×10$^8$, 1:1×10$^9$ or 1:1×10$^{10}$. In some embodiments, the composition comprises a mixture of primer extension products that are complementary to a ss polynucleotide library comprising an adapter on at least one end of a sequence derived from genomic DNA, cDNA or RNA; and a terminal transferase. In some embodiments, the composition further comprises a polymerase. In some embodiments, the composition further comprises dNTPs.

In certain aspects, provided herein is a method for identifying the number of unique molecules in a nucleic acid sample, the method comprising performing the method described herein to label a library of polynucleotide with unique variable sequences; amplifying the library of polynucleotide molecules; and sequencing the unique variable sequence.

In certain aspects, provided herein is a kit for performing a method described herein. In some embodiments, the kit comprises a nucleic acid molecule encoding a 5' adapter sequence and oligonucleotides comprising, in 3' to 5' order, a non-extendable 3' end, a sequence capable of hybridizing to the 3' terminal region a sequence complementary to the 5' adapter sequence and a variable barcode sequence. In some embodiments, the kit further comprises a nucleic acid molecule encoding a 3' adapter sequence and a sample index primer comprising, in 5' to 3' order, a sample-specific barcode sequence and a sequence capable of hybridizing to at least a portion of the 3' adapter sequence. In some embodiments, the kit further comprises a first primer capable of hybridizing to a sequence complementary to a sequence of the sample index primer located 5' of the sample-specific barcode sequence and a second primer capable of hybridizing to a sequence complementary to a sequence of the oligonucleotides located 5' of the variable barcode sequence.

In any of the above methods, compositions or kits, the 5' end of the synthetic oligonucleotide may be protected from exonuclease digestion. In some embodiments, the second adapter comprises one or more deoxyuridines.

In certain embodiments, a hybridization sequence described herein is capable of hybridizing "under stringent conditions" to another sequence. Stringent hybridization conditions include, for example, hybridization in 6× sodium chloride/sodium citrate (SSC) at about 45° C., followed by one or more washes in 0.2×SSC, 0.1% SDS at 50° C.-65° C.

BRIEF DESCRIPTION OF THE FIGURES

FIG. 1A-1F shows an exemplary method for adding degenerate sequences that serve as unique identifiers to polynucleotides according to certain embodiments described herein.

FIG. 1A shows a library of polynucleotide molecules, containing 3' (1) and 5' (2) adapter sequences is melted to form a ss polynucleotide library. (3) represents the captured polynucleotide fragment.

FIG. 1B shows a primer (optionally including a sample index) (4) that hybridizes to the 3' adapter sequence of the library ss polynucleotide. (5) represents the region of the ds polynucleotide that is hybridized to the 3' end of the sample primer (4).

FIG. 1C shows a duplex formed by polymerase dependent primer extension. The library polynucleotide serves as a template for the extension resulting in the formation of a duplex. The newly formed duplex now includes a primer extension product containing the primer sequence, a sequence complementary to at least a portion of the 3' adapter, a sequence complementary to the target polynucleotide and a sequence complementary to the 5' adapter sequence (6) refers to the polymerase synthesized polynucleotide complement to the library polynucleotide sequence and the 5' adapter. sequence.

FIG. 1D shows the denatured duplex which is combined with an excess of an oligonucleotide (UID template) (10). The oligonucleotide hybridizes to the 3' end of the primer extension sequence (i.e., to a sequence complementary to the 5' adapter sequence) (7). The oligonucleotide contains a variable barcode sequence (a UID) (8) located 5' to the hybridization sequence. (9) refers to the non extendable 3' end.

FIG. 1E shows the extension of the primer extension product to incorporate the variable barcode sequence. This product may be heat denatured and additional rounds of second strand extension performed. (11) represents the newly synthesized polynucleotide (polymerase dependent). (12) represents the non extendable 3' end.

FIG. 1F shows amplification of the ss primer extension product from FIG. 1E that is the product of extension incorporating complementary sequence to the non hybridizing UID template sequence using, for example, PCR. (13) represents the primer pair used for PCR.

FIG. 2A-2G shows an exemplary method for adding degenerate sequences that serve as unique identifiers to DNA according to certain embodiments described herein.

FIGS. 2A, 2B and 2C are the same as in FIGS. 1A, 18 and 1C.

FIG. 2D shows the product of 5' exonuclease digestion from the 5' end of the library polynucleotide strand in the duplex while the primer extension product remains and is undigested due to the exonuclease protected 5' end. (14) represents the exonuclease protected end. (15) represents the 5'exonuclease digested region.

FIG. 2E shows an addition of an excess of an oligonucleotide that hybridizes to the 3' end of the primer extension sequence (i.e., to a sequence complementary to the 5' adapter sequence). The oligonucleotide contains a variable barcode sequence (a UID) located 5' to the hybridization sequence.

FIG. 2F shows how the primer extension product is further extended to incorporate the variable barcode sequence. This product may be heat denatured and additional rounds of second strand extension performed.

FIG. 2G shows amplification of the primer extension product using, for example, PCR.

FIG. 3A-3G provides exemplary nucleic acid sequences from certain embodiments of the methods and compositions described herein.

FIG. 3A shows an exemplary member of a DNA library that includes an exemplary 3' adapter sequence (the Read 2 sequencing primer sequence, SEQ ID NO:1) and an exemplary 5' adapter sequence (the Read 1 sequencing primer sequence, SEQ ID NO:2).

FIG. 3B shows an exemplary Sample Index Primer sequence (SEQ ID NO:3) aligned with the exemplary member of a DNA library. A sample identifier sequence is shown (index).

P7 identifies the P7 primer recognition sequence.

FIG. 3C shows an exemplary primer extension product sequence (SEQ ID NO:3 and SEQ ID NO:4) aligned with the exemplary member of a DNA library.

FIG. 3D The exemplary primer extension product sequence (SEQ ID NO:3, SEQ ID NO:4) aligned with the sequence of the exemplary member of a DNA library following 5' exonuclease digestion (SEQ ID NO:1).

FIG. 3E shows the 3' terminal region of the exemplary primer extension product sequence (SEQ ID NO: 4) aligned with an exemplary oligonucleotide containing a degenerate barcode sequence (NNNNNNNN) (SEQ ID NO:5). P5 represents the P5 primer recognition sequence.

FIG. 3F shows the 3' terminal region of an exemplary primer extension product sequence (SEQ ID NO:6) following performance of a further extension step aligned with exemplary oligonucleotide containing a degenerate barcode sequence (NNNNNNNN) (SEQ ID NO:5).

FIG. 3G shows the exemplary further extended primer extension product sequence (SEQ ID NO:6, SEQ ID NO:3) aligned with a first PCR primer (PCR1, SEQ ID NO:8) and a second PCR primer (PCR2, SEQ ID NO:7).

FIG. 4A-4F shows an exemplary method for adding degenerate sequences that serve as unique identifiers to polynucleotides according to certain embodiments described herein in which a terminal transferase is used to add random sequence to the 3' end of an extension product generated from a polynucleotide library.

Figure 4A:

FIG. 4A shows a sample from a library of polynucleotide molecules with a 3' adapter and, optionally, a 5' adapter.

Figure 4B:

FIG. 4B shows hybridization of a primer to the 3' adapter sequence. The primer may optionally include a sample-specific barcode sequence.

Figure 4C:
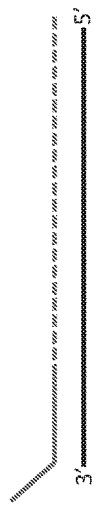
Figure 4D:
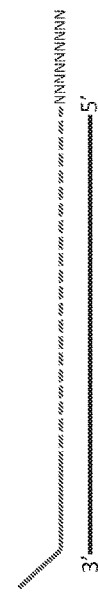

FIG. 4C shows extension of the primer to produce a primer extension product which is hybridized to the sample polynucleotide such that the 3' end of the primer extension product forms a blunt end with the 5' end of the sample polynucleotide FIG. 4D shows that the 3' end of the primer extension product is further extended by a terminal transferase, which adds an untemplated random sequence to the 3' end of the primer extension product. This untemplated random sequence can serve as a molecule-specific barcode (a UID).

Figure 4E:
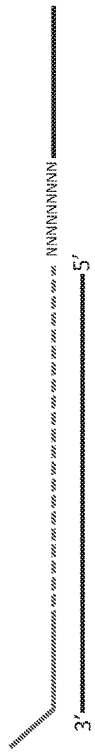

FIG. 4E shows how a ss DNA adapter is ligated to the 3' end of the primer extension sequence.

Figure 4F:
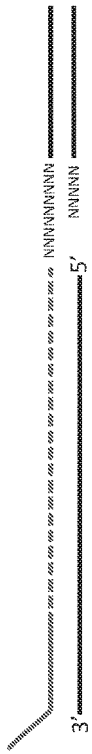

FIG. 4F provides an alternative to FIG. 4E. A ds DNA adapter is ligated to the untemplated random sequence, with the ds adapter including a random sequence on one strand can hybridize to the random sequence added to the primer extension product by the terminal transferase.

FIG. 5A-5E shows an exemplary method for adding degenerate sequences that serve as unique identifiers to DNA according to certain embodiments described herein in which a terminal transferase is used to add random sequence to the 3' end of an extension product generated from a DNA library.

Figure 5A:

FIG. 5A shows a library of polynucleotide molecules with a 3' adapter and a 5' adapter. The 5' adapter is a synthetic oligonucleotide that contains modified nucleotides that can terminate replication by a DNA polymerase (an unreplicable sequence).

Figure 5B:

FIG. 5B shows how a primer hybridizes to the 3' adapter sequence. The primer may optionally include a sample-specific barcode sequence.

Figure 5C:
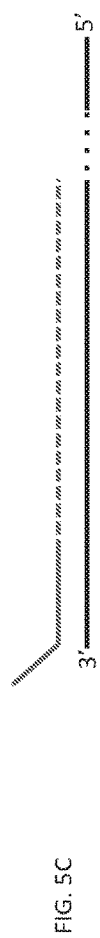

FIG. 5C shows that the primer can be extended up to the unreplicable sequence to produce a primer extension product.

Figure 5D:
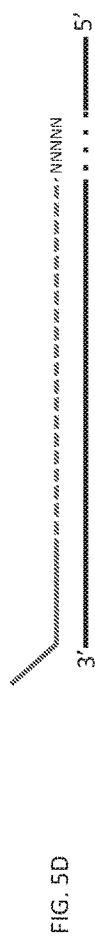

FIG. 5D shows extension of the 3' end of the primer extension product by a terminal transferase, which adds an untemplated random sequence to the 3' end of the primer extension product. This untemplated random sequence can serve as a molecule-specific barcode (a UID). The sequence added by the terminal transferase bridges the unreplicable region.

Figure 5E:
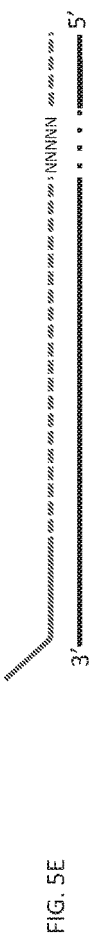

FIG. 5E shows that the polymerase further extends the primer extension product to incorporate a sequence complementary to the remainder of the 5' adapter.

DESCRIPTION OF TERMS

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections), from preserved tissue (such as FFPE sections) or from in vitro cell culture constituents, as well as samples from the environment. DNA molecules of interest include genomic DNA, (which could be from the nucleus or organelle of a cell, or from the genome of a virus), and RNA molecules of interest include messenger RNAs (mRNAs), microRNAs (miRNAs), long non coding RNAs (lncRNAs), ribosomal RNAs (rRNAs), transfer RNAs (tRNAs) and the genome of an RNA virus, etc., which RNAs may be copied to cDNA, if required.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically.

The term "nucleic acid sample," as used herein denotes a sample containing nucleic acids. A nucleic acid samples used herein may be complex in that they contain multiple different molecules that contain sequences. Genomic DNA, and cDNA samples from a mammal (e.g., mouse or human) are types of complex samples. Complex samples may have more than $10^4$, $10^5$, $10^6$ or $10^7$ different nucleic acid molecules. Also, a complex sample may comprise only a few molecules, where the molecules collectively have more than $10^4$, $10^5$, $10^6$ or $10^7$ or more nucleotides. A DNA target may originate from any source such as genomic DNA, cDNA or an artificial DNA construct. Any sample containing nucleic acid, e.g., genomic DNA, cDNA or RNA made from tissue culture cells or a sample of tissue, may be employed herein.

The term "library of polynucleotide molecules" as used herein may be complex in that it contains multiple different molecules. Genomic DNA, and cDNA samples from a mammal (e.g., mouse or human) are types of complex samples. Complex samples may have more than $10^4$, $10^5$, $10^6$ or $10^7$ different nucleic acid molecules. Also, a complex sample may comprise only a few molecules, where the molecules collectively have more than $10^4$, $10^5$, $10^6$ or $10^7$ or more nucleotides. A polynucleotide (or nucleic acid) may originate from any source such as genomic DNA, cDNA or an artificial DNA construct or from mRNA, microRNAs, long non-coding RNAs or other RNAs of interest. In some embodiments, a library of polynucleotide molecules may be an enriched library, in which case the library may have a complexity of less than 10%, less than 5%, less than 1%, less than 0.5%, or less than 0.1%, less than 0.01%, less than 0.001% or less than 0.0001% relative to the unenriched sample (e.g., a sample made from total RNA or total genomic DNA from a eukaryotic cell sample. Molecules can be enriched by methods such as described in US2014/0287468 or US 2015/0119261.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the likes.

The term "oligonucleotide" as used herein denotes a ss multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "mixture", as used herein, refers to a combination of elements, that are interspersed and not in any particular order. Examples of mixtures of elements include a number of different elements that are dissolved in the same aqueous solution. A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length. As noted below, a primer may be "tailed" in the sense that the 3' end of the primer may hybridize to a target sequences and the 5' end of the primer may not hybridize to the target sequence. The term "tailed", in the context of a tailed primer or a primer that has a 5' tail, refers to a primer that has a region (e.g., a region of at least 12-50 nucleotides) at its 5' end that does not hybridize to the same target as the 3' end of the primer.

Primers are usually ss for maximum efficiency in amplification, but may alternatively be ds, e.g., in the shape of a hairpin. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

An "oligonucleotide binding site" or "hybridization sequence" refers to a site to which an oligonucleotide hybridizes in a target polynucleotide. If an oligonucleotide "provides" a binding site or hybridization sequence for a primer, then the primer may hybridize to that oligonucleotide or its complement.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, Pacific Bio, and Roche etc.

Next-generation sequencing methods may also include nanopore sequencing methods or electronic-detection based methods such as Ion Torrent technology commercialized by Life Technologies.

The term "strand" as used herein refers to a nucleic acid made up of nucleotides covalently linked together by covalent bonds, e.g., phosphodiester bonds. In a cell, DNA usually exists in a ds form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "hybridizing" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double strandedness under normal stringency conditions, unless the two nucleic acid strands contain a certain number of nucleotides in specific sequences which are substantially or completely complementary.

The term "extending", as used herein, refers to the extension of a nucleic acid, e.g., a primer or a primer extension product, by the addition of nucleotides using a polymerase. For example, if a primer that is annealed to a nucleic acid is extended, the nucleic acid acts as a template for extension reaction.

The term "not extendible", in the context of an oligonucleotide that is not extendible at its 3' end when it is annealed to a target nucleic acid, refers to an oligonucleotide that cannot be extended by a template polymerase-dependent polymerase, either because the 3' end of the oligonucleotide is blocked at the 3' end (e.g., by a dideoxy nucleotide or any of a multitude of nucleotides that are not substrates for the polymerase) or because the 3' end of the oligonucleotide is mis-matched with the target, i.e., because one or more nucleotides at the 3' end of the oligonucleotide are not complementary to correspondingly positioned nucleotides in the target sequence).

The term "adapter" refers to a sequence that is joined to or can be joined to another molecule (e.g., ligated or copied onto via primer extension). An adapter can be DNA or RNA, or a mixture of the two. An adapter may be 15 to 100 bases, e.g., 50 to 70 bases, although adapters outside of this range are envisioned. In a library of polynucleotide molecules that contain an adapter (e.g., a 3' or 5' adapter, the adapter sequence used is not present in the DNA sequences under examination (i.e., the sequence in between the adapters). For example, if the library of polynucleotide molecules contains sequences derived from mammalian genomic DNA, cDNA or cDNA, then the sequences of the adapters are not present in the mammalian genome under study. In many cases, the 5' and 3' adapters are of a different sequence and are not complementary. In many cases, an adapter will not contain a contiguous sequence of at least 8, 10 or 12 nucleotides that is found in the DNA under examination.

The term "adapter-containing", in the context of an adapter-containing nucleic acid, refers to either a nucleic acid that has been ligated to an adapter, or to a nucleic acid to which an adapter has been added by primer extension. In some embodiments, the adapters of a library of nucleic acid molecules may be made by ligating oligonucleotides to the 5' and 3' ends of the molecules (or specific sequences of the same) in an initial nucleic acid sample, e.g., DNA or genomic DNA, cDNA.

The term "formed from", in the context of the primer extension products that is "formed from" genomic DNA, cDNA or RNA, refers to primer extension products that are copied from template genomic DNA, cDNA or RNA, or the complement thereof. Such primer extension products are usually DNA.

The term "sample index primer" is a primer that contains a sample identifier sequence, i.e., a sequence that can be used to identify and/or track the source of a polynucleotide in a reaction. In some embodiments, several different samples may be pooled together before sequencing and each is tagged with a different sample identifier sequence. After sequencing, the sample identifier sequence in the sample index primer can be identified in the sequence reads, and the source of the sequence read (e.g., which sample) can be determined. In use, each samples may be tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences. In many cases, each sample may be tagged with a single sample identifier sequence, i.e., a sequence that is unique to the sample.

The term "variable barcode sequence" refers to as used herein, refers to a molecular barcode that varies in sequence in a population of oligonucleotides. In some cases, a population of oligonucleotides may contain a high complexity variable barcode sequence, in which case, the oligonucleotide may contain a degenerate sequence made up of at least 10,000, at least 100,000 or at least 1M different sequences. In other embodiments, the population of oligonucleotides may contain a low complexity variable barcode sequence. In these embodiments, the oligonucleotide may have a region composed of less than 10,000, less than 1,000 or less than 100 sequences. In these embodiments, some primer extension products may be tagged with the same barcode sequence, but those fragments can still be distinguished by other metrics, e.g., the sequence of the fragment, the sequence of the ends of the fragment etc. In some embodiments, at least 95%, e.g., at least 96%, at least 97%, at least 98%, at least 99% or at least at least 99.5% of the target polynucleotides become associated with a different barcode sequence. Such variable barcode sequences may vary widely in size and composition; the following references provide guidance for selecting sets of variable barcode sequences appropriate for particular embodiments: Casbon, Nuc. Acids Res., 22 e81 (2011); Brenner, U.S. Pat. No. 5,635,400; Brenner, et al., Proc. Natl. Acad. Sci., 97: 1665-1670 (2000); Shoemaker, et al., Nature Genetics, 14: 450-456 (1996); Morris, et al., European patent publication 0799897A1; Wallace, U.S. Pat. No. 5,981,179; and the like. In particular embodiments, a variable barcode sequence may have a length in range of from 4 to 36 nucleotides, or from 6 to 30 nucleotides, or from 8 to 20 nucleotides. In some cases, an oligonucleotide with a variable barcode sequence can be made by synthesizing an oligonucleotide that contains a degenerate sequence (e.g., an oligonucleotide that has a run of 4-10 "Ns", where "N" is G, A, T or C, or any combination thereof).

A variable barcode sequence can be used to correct sequencing errors and to count how many times an initial molecule is sequenced (e.g., in cases where substantially every molecule in a sample is tagged with a different sequence, and then the sample is amplified). See, e.g., Casbon, Nuc. Acids Res., 22 e81(2011).

Among other things, e.g., correcting sequence/PCR errors, allele calling, etc., a variable barcode sequence can be used to determine the number of initial target polynucleotide molecules that have been analyzed, i.e., to "count" the number of initial target polynucleotide molecules that have been analyzed. PCR amplification of molecules that have been tagged with a variable barcode sequence results in multiple sub-populations of products that are clonally-related in that each of the different sub-populations is amplified from a single tagged molecule. As would be apparent, even though there may be several thousand or millions or more or molecules in any of the clonally-related sub-populations of PCR products and the number of target molecules in those clonally-related sub-populations may vary greatly, the number of molecules tagged in the first step of the method can be estimated by counting the number of variable barcode sequences associated with a target sequence that is represented in the population of PCR products. This number is useful because, in certain embodiments, the population of PCR products made using this method may be sequenced to produce a plurality of sequences. The number of different variable barcode sequences that are associated with the sequences of a target polynucleotide can be counted, and this number can be used (along with, e.g., the sequence of the fragment, the sequence of the ends of the fragment) to estimate the number of initial template nucleic acid molecules that have been sequenced.

Other descriptions of terms may appear throughout the specification.

DETAILED DESCRIPTION

Provided herein are methods and compositions for labeling target nucleic acid molecules with molecular barcodes (e.g., with sample-specific barcodes and/or with molecule-specific barcodes). In some embodiments, the molecules are labeled one and only one time. In some embodiments, the individual original molecules more than one time (e.g. in a streamlined procedure).

In some embodiments, the methods and compositions described herein relate to the labeling of a library of polynucleotide molecules with a molecular barcode. In some embodiments, the library of polynucleotide molecules comprise a first (3') adapter and a sequence derived from genomic DNA, cDNA or RNA (e.g., a cDNA library). In some embodiments, the library of polynucleotide molecules also includes a second (5') adapter. In some embodiments, the 5' adapter includes an unreplicable region. Modified nucleotides that cannot typically be replicated by DNA polymerases include xanthosine, 3-nitropyrrole, 5-nitroindole, or any C-glycosidic nucleotide analogs. In some embodiments, the library is a ss polynucleotide library. In some embodiments, the library of polynucleotide molecules is a complete genomic DNA library or a complete mRNA/cDNA library. In some embodiments, the library of polynucleotide molecules is a target-enriched genomic DNA, library or a target-enriched mRNA/cDNA library.

In some embodiments, the genomic DNA, cDNA or mRNA/cDNA library is generated from the DNA or RNA of a human or a non-human animal. In some embodiments, the non-human animal is a mammal (e.g., a cow, pig, horse, donkey, goat, camel, cat, dog, guinea pig, rat, mouse, sheep, monkey, gorilla, chimpanzee). In some embodiments, the genomic DNA, or mRNA/cDNA library is human.

In certain embodiments, the initial DNA being analyzed may be derived from a single source (e.g., a single organism, virus, tissue, cell, subject, etc.), whereas in other embodiments, the nucleic acid sample may be pooled with other samples that are from a plurality of sources, where by "plurality" is meant two or more. As such, in certain embodiments, after pooling a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. A sample identifier sequence may be added to each of the sources prior to pooling, and the sequence can allow the sequences from different sources to be distinguished after they are analyzed.

In some embodiments, the DNA or mRNA/cDNA library is generated using DNA fragments obtained from a clinical sample, e.g., a patient that has or is suspected of having a disease or condition such as a cancer, inflammatory disease or pregnancy. In some embodiments, the sample may be made by extracting fragmented DNA from an archived patient sample, e.g., a formalin-fixed paraffin embedded tissue sample. In other embodiments, the patient sample may be a sample of cell-free circulating DNA from a bodily fluid, e.g., peripheral blood. In some embodiments, the DNA in the initial sample may already be fragmented (e.g., as is the case for FFPE samples and circulating cell-free DNA (cfDNA), e.g., ctDNA). The fragments in the initial sample may have a median size that is below 1 kb (e.g., in the range of 50 bp to 500 bp, 80 bp to 400 bp, or 100-1,000 bp), although fragments having a median size outside of this range may be used. Cell-free or circulating tumour DNA (ctDNA), i.e., tumour DNA circulating freely in the blood of a cancer patient, is highly fragmented, with a mean fragment size about 165-250 bp (Newman, et al., Nat Med. 2014 20: 548-54). cfDNA can be obtained by centrifuging whole blood to remove all cells, and then analyzing the remaining plasma.

The polynucleotide libraries described herein can be generated using methods described herein or otherwise known in the art. For example, in some embodiments, genomic DNA, cDNA or RNA is fragmented into small ds polynucleotide fragments followed by ligation of adapters to the ends of the polynucleotide fragments. Where mRNA is the source of the library of target DNA to be analyzed, cDNA formed by reverse transcriptase is ligated to adapters. As used herein, the term "adapter" refers to a region of known sequence located either 3' or 5' of a target DNA sequence in a DNA library. In some embodiments, an adapter is at least 10, 15, 20, 30, 40, 50, 60, or 70 nucleotides in length. When both 3' adapters and 5' adapters are used, the 3' adapters preferably have different sequences from the 5' adapters. Exemplary library preparation methods are described in US 2014/02867468, U.S. patent application Ser. No. 13/513,726 and U.S. Pat. No. 8,288,097, each of which is hereby incorporated by reference. Target enriched libraries described in US 2014/02867468, which is hereby incorporated by reference.

In some embodiments, a primer extension product (also referred to as a second strand DNA) is made from the library of polynucleotide molecules.

In some embodiments, the primer extension product is made such that the library of polynucleotide molecules is labeled with a library-specific barcode sequence located 5' of the sequence complementary. In some embodiments, the primer extension product is made by contacting the library of polynucleotide molecules with sample index primers, the sample index primers comprising, in 5' to 3' order, a sample-specific barcode sequence and a first hybridization sequence, such that the first hybridization sequence hybridizes to a region of the first adapter of the library of polynucleotide molecules and then incubating the hybridized DNA molecules with a polymerase such that the polymerase extends 3' end of the sample index primers to form primer extension products comprising, in 5' to 3' order, a sample-specific barcode sequence, a sequence complementary to at least a portion of the first adapter, a sequence complementary to the genomic DNA, cDNA or mRNA derived sequence, and a sequence complementary to the second adapter. As used herein, the terms "hybridize" or "hybridization" refer to the hydrogen bonding of complementary or substantially complementary DNA and/or RNA sequences to form a duplex molecule. In some embodiments, a nucleic acid sequence is referred to as being "capable of hybridizing" to another nucleic acid sequence if there is at least about 65%, at least 75% or at least 90% sequence complementary over a stretch of at least 14 nucleotides to 25 nucleotides. In some embodiments, "a sequence capable of hybridizing" or a "hybridization sequence" is complementary to a target sequence and is at least 8, 10, 11, 12, 13, 14, 15, 16, 17, 18, 19, 20, 40, or 60 nucleotides in length.

Primer extension products are generated by use of a primer. The term "primer" as used herein refers to an oligonucleotide that is capable, upon forming a duplex with a polynucleotide template, of acting as a point of initiation of nucleic acid synthesis and being extended from its 3' end along the template so that an extended duplex is formed. Usually primers are extended by a mesophilic DNA polymerase, such as Klenow, Klenow (exo-), Bsu, or DNA polymerase I or a thermophilic DNA polymerase such as Taq, KlenTaq®, Tth, Bst, Bst (large fragment), Vent®, Deep Vent®, Q5®, and Phusion® (all commercially available from New England Biolabs, Ipswich, Mass.). Primers can be ss, ds, or partially ss and partially ds. If ds, the primer is generally first treated to separate its strands before being used to prepare extension products. This denaturation step is typically affected by heat, but may alternatively be carried out using alkali, followed by neutralization. Thus, a primer has at least a 3' sequence complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

In some embodiments, primers described herein are designed such that its 3' end hybridizes to a 3' adapter leaving a 5' tail. 5' of the region capable of hybridizing to the 3' adapter the primer may include a non-random index sequence (a MID). In some embodiments, the MID is 2-15 nucleotides in length for example 6-10 nucleotides for example, 8 nucleotides. In some embodiments, the primer further includes a platform specific sequencing tag 5' of the MID and/or the adapter hybridization sequence. The MID may be positioned between the platform specific sequencing tag and the adapter hybridization sequence. An example of a platform specific tag is an Illumina sequence tag for MiSEQ® such as P7 (Illumina, San Diego, Calif.). The MID can be used to identify each sample in a pool of samples sequenced together in one run on a multiplex sequencing platform.

In some embodiments, a ds molecule comprising the primer extension product and the DNA library template is formed during a primer extension process. In some embodiments, this ds molecule is denatured into ss and then contacted with a UID-template oligonucleotide. In some embodiments, the ds molecule is treated with a 5' exonuclease that digests the 5' end of the original DNA library molecule. In such embodiments, the 5' end of the primer extension product is protected from exonuclease digestion (e.g., through the absence of a 5' phosphate or the presence of a blocking nucleotide).

In some embodiments, the primer extension product is labeled by contacting primer extension products with UID-template oligonucleotides. In some embodiments, the UID-template oligonucleotides include, in 3' to 5' order, a non-extendable 3' end, a second hybridization sequence, and a variable barcode sequence (e.g., a degenerate random sequence of 2-15 nucleotides, 6-10 nucleotides or 8 nucleotides) such that the second hybridization sequence hybridizes to a 3' terminal region of the sequence complementary to the second adapter and then incubating the hybridized primer extension products with a polymerase such the polymerase extends the 3' end of the primer extension products to form a further extended primer extension product comprising, in 5' to 3' order, the sequence complementary to at least a portion of the first adapter, the sequence complementary to the genomic DNA, cDNA or mRNA derived sequence, the sequence complementary to the second adapter, and a sequence complementary to the variable barcode sequence of the oligonucleotide. The UID-template oligonucleotide may also include a 5' commercial platform sequence tag. The UID-template oligonucleotide can be used in a ratio to target of 1:1 to $1 \times 10^{12}$, or less than 1:1 or more than $1 \times 10^{12}$. Mesophilic polymerases useful in the further extension of the primer extension product include Klenow, Klenow (exo-), Bsu, or DNA polymerase I or thermophilic DNA polymerases such as Taq, KlenTaq, Tth, Bst, Bst (large fragment), Vent, Deep Vent, Q5, or Phusion.

In some embodiments, a barcode-labeled product is amplified (e.g., using PCR). Examples of nucleic acid amplification processes that can be used include, but are not limited to, polymerase chain reaction (PCR), ligase chain reaction (LCR), strand displacement amplification (SDA), transcription mediated amplification (TMA), self-sustained sequence replication (3SR), Qβ replicase based amplification, nucleic acid sequence-based amplification (NASBA), repair chain reaction (RCR), boomerang DNA amplification (BDA) and/or rolling circle amplification (RCA).

In some embodiments of the methods described herein, a sequencing process is performed on the barcode-labeled product. In some embodiments, the sequencing process is a multiplex sequencing process. Nucleic acid sequencing processes include, but are not limited to chain termination sequencing, sequencing by ligation, sequencing by synthesis, pyrosequencing, ion semiconductor sequencing, single-molecule real-time sequencing, 454 sequencing, and/or Dilute-'N'-Go sequencing.

In some embodiments, the sequencing process is a NGS process. NGS platforms include, but are not limited to, Massively Parallel Signature Sequencing (Lynx Therapeutics, Hayward, Calif.); 454 pyrosequencing (454 Life Sciences/Roche Diagnostics, Branford, Conn.); solid-phase, reversible dye-terminator sequencing (Solexa/Illumina, San Diego, Calif.); SOLID® technology (Applied Biosystems/Life Technologies, Grand Isle, N.Y.); Ion semiconductor sequencing (Ion Torrent™, Life Technologies, Grand Isle, N.Y.); and DNA nanoball sequencing (Complete Genomics, Mountain View, Calif.). Descriptions of certain NGS platforms can be found in the following: Shendure, et al., *Nature*, 26:1135-1145 (2008); Mardis, *Trends in Genetics*, 24:133-141 (2007); Su, et al., *Expert Rev Mol Diagn*, 11(3):333-43 (2011); and Zhang et al., *J Genet Genomics*, 38(3):95-109 (2011), each of which are hereby incorporated by reference.

In some embodiments, provided herein is a kit for performing a method described herein. The term "kit" refers to any delivery system for delivering materials or reagents for carrying out a method described herein. In some embodiments, such delivery systems can include systems that allow for the storage, transport, or delivery of reaction reagents (e.g., probes, enzymes, adapters, primers etc. in the appropriate containers) and/or supporting materials (e.g., buffers, written instructions for performing the assay etc.) from one location to another. For example, in some embodiments kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes. A kit may be formulated for selecting and enriching target templates from a nucleic acid sample containing non-target and target sequences. The kit may include one or more primers as described herein adapters; nucleases; ligase; polymerase(s); buffers; and nucleotides. The kit may further comprise one or more buffer solutions and standard solutions for the creation of a DNA library.

In some embodiments, a terminal transferase is used to generate degenerate sequences for molecule identification (UIDs). For example, as illustrated in FIG. 4, in some embodiments primer extension products of original DNA library molecules are further extended by terminal transferase, generating a random sequence at the 3' end of the primer extension product, which extends beyond the 5' end of the original DNA library molecule in a random manner. A ss adapter can then be attached to the 3' end of the extension product or alternatively be introduced through a ds adapter having a random sequence at the 3' end of the second strand. As illustrated in FIG. 5, in some embodiments the terminal transferase forms a bridge over an unreplicable region of a 5' adapter of the original DNA library molecule, thereby permitting further extension of the primer extension product. Modified nucleotides that cannot typically be replicated by DNA polymerases include xanthosine, 3-nitropyrrole, 5-nitroindole, or any C-glycosidic nucleotide analogs.

The term "non-naturally occurring" refers to a composition that does not exist in nature. In the context of a nucleic acid, the term "non-naturally occurring" refers to a nucleic acid that contains: a) a sequence of nucleotides that is different to a nucleic acid in its natural state, b) one or more non-naturally occurring monomers (which may result in a non-natural backbone or sugar that is not G, A, T or C) and/or C) may contain one or more other modifications (e.g., an added label or other moiety) to the 5'-end, the 3'-end, and/or between the 5'- and 3'-ends of the nucleic acid.; c) a combination of sequences that would not occur together in nature but here have been synthesized enzymatically or by chemical synthesis.

In the context of a composition or preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that not found in nature, e.g., dried, freeze dried, crystalline, aqueous; e) a combination that contains a component that is not found in nature. For example, a preparation may contain a buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature and/or (f) the combination is contained in a non-cell container such as a reaction vessel, where the term reaction vessel refers to a tube, or well in which reagents may be in solution or immobilized where immobilization may occur on the surface of the reaction vessel or on a bead in the reaction vessel.

All references cited herein are incorporated by reference.

EMBODIMENTS

In some embodiments the method may comprise: (a) hybridizing a library of polynucleotide molecules comprising, in 3' to 5' order, a first adapter, a sequence derived from genomic DNA, cDNA or RNA, and a second adapter with a sample index primer, the sample index primer comprising, in 5' to 3' order, a sample-specific barcode sequence and a first hybridization sequence, wherein the first hybridization sequence hybridizes to a region of the first adapter; (b) incubating the hybridized polynucleotide molecules formed in step (a) with a polymerase such that the polymerase extends the 3' end of the sample index primer to form primer extension products comprising, in 5' to 3' order, a sample-specific barcode sequence, a sequence complementary to at least a portion of the first adapter, a sequence complementary to the genomic DNA, cDNA or RNA derived sequence, and a sequence complementary to the second adapter; (c) hybridizing the primer extension products formed in step (b) with synthetic oligonucleotides comprising, in 3' to 5' order, a non-extendable 3' end, a second hybridization sequence, and a variable barcode sequence, wherein the second hybridization sequence hybridizes to a 3' terminal region of the sequence complementary to the second adapter; (d) incubating the hybridized primer extension products of step (c) with a polymerase such the polymerase extends the 3' end of the primer extension products to form a further extended primer extension product; and (e) optionally amplifying the further extended primer extension products formed in (d).

In some embodiments, the method further comprising the step of denaturing the primer extension products from the polynucleotide molecules between steps (b) and (c).

In some embodiments, the method further comprising removing a 5' terminal sequence from the polynucleotide molecules of the library after step (b) and prior to step (c), leaving a 3' overhang.

In some embodiments, the 5' terminus of the sample index primer is protected from exonuclease digestion and the 5' terminal sequence of the polynucleotides molecules of the library is removed by an exonuclease.

In some embodiments, the second adapter comprises one or more deoxyuridines, and the 5' terminal sequence of the polynucleotides molecules of the library is removed using uracil DNA glycosylase (UDG) and DNA endonuclease VIII.

In some embodiments, step (d) further comprises amplifying by PCR the further extended primer extension product.

In some embodiments, the method further comprises the step of performing a sequencing process on the amplification products.

In some embodiments, the method further comprises performing the method to label a library of polynucleotide molecules with unique variable sequences; amplifying the library of polynucleotide molecules; and sequencing the unique variable sequence.

In some embodiments, the method comprises: (a) hybridizing primer extension products with synthetic oligonucleotides, wherein: (i) the primer extension products are formed from a library of polynucleotide molecules comprising, in 3' to 5' order, a first adapter, a sequence derived from genomic DNA, cDNA or RNA, and a second adapter; (ii) the primer extension products comprise, in 5' to 3' order, a sequence complementary to at least a portion of the first adapter, a sequence complementary to the genomic DNA, cDNA or RNA derived sequence, and a sequence complementary to the second adapter; (iii) the synthetic oligonucleotides comprise, in 3' to 5' order, a non-extendable 3' end, a hybridization sequence, and a variable barcode sequence; and (iv) the hybridization sequence hybridizes to a 3' terminal region of the sequence complementary to the second adapter; (b) incubating the hybridized primer extension products of step (a) with a polymerase such the polymerase extends the 3' end of the primer extension products to form a further extended primer extension product; and (c) optionally amplifying the further extended primer extension products formed in (b).

In some embodiments, the method may further comprise the steps of: hybridizing the library of polynucleotide molecules with primers comprising a 3' terminal first adapter hybridization sequence, wherein the first adapter hybridization sequence hybridizes to a region of the first adapter; and incubating the resulting hybridized polynucleotide molecules with a polymerase such that the polymerase extends 3' end of the primers to form the primer extension products prior to step (a).

In some embodiments, the method further comprise the step of denaturing the primer extension products from the polynucleotide molecules prior to step (a).

In some embodiments, the 5' terminus of the primer is protected from exonuclease digestion and further comprising the step of incubating primer extension product and the DNA molecules with a 5' exonuclease such that a 5' terminal sequence is removed from the DNA molecules of the library prior to step (c).

In some embodiments, the second adaptor contains modified nucleotides that allow only partial digestion by a 5' exonuclease.

In some embodiments, the modified nucleotides are internal phosphothioates.

In some embodiments, the 5' exonuclease removes 10-20 bases from an end of the second adaptor leaving a single strand overhang.

In some embodiments, the method further comprises removing a 5' terminal sequence from the polynucleotide molecules of the library after step (b) and prior to step (c), leaving a 3' overhang.

In some embodiments, the method further comprises amplifying by PCR the further extended primer extension product.

In some embodiments, the method further comprises performing the method to label a library of polynucleotide molecules with unique variable sequences amplifying the library of polynucleotide molecules; and sequencing the unique variable sequence.

In some embodiments, the method may comprise: (a) hybridizing a library of polynucleotide molecules comprising, in 3' to 5' order, a first adapter, a sequence derived from genomic DNA, cDNA or RNA, and a second adapter comprising an unreplicable region with primers comprising a 3' terminal first adapter hybridization sequence, wherein the first adapter hybridization sequence hybridizes to a region of the first adapter; (b) incubating the hybridized polynucleotide molecules formed in step (a) with a polymerase such that the polymerase extends 3' end of the primers to form primer extension products comprising, in 5' to 3' order, a sequence complementary to at least a portion of the first adapter, a sequence complementary to the genomic DNA, cDNA or RNA derived sequence, and a sequence complementary to the portion of the second adapter that is 3' of the unreplicable region; (c) incubating the products of step (b) with a 3' terminal transferase such that a random nucleic acid sequence is added to the 3' terminus of the primer extension products; and (d) incubating the products of step (c) with a polymerase such the polymerase further extends the primer extension products to form a further extended primer extension product comprising, in 5' to 3' order, the sequence complementary to at least a portion of the first adapter, the sequence complementary to the genomic DNA, cDNA or RNA derived sequence, the sequence complementary to the portion of the second adapter that is 3' of the unreplicable region, the random nucleic acid sequence, and a sequence complementary to a portion of the second adapter that is 5' of the unreplicable region.

In some embodiments, the method further comprises the step of amplifying the further extended primer extension product formed in step (d).

In some embodiments, the method comprises performing the method to label a library of polynucleotide molecules with unique variable sequences, wherein step (e) further comprises amplifying the library of polynucleotide molecules; and sequencing the unique variable sequence.

In some embodiments, the method may comprise: (a) hybridizing a library of polynucleotide molecules comprising, in 3' to 5' order, a first adapter and a sequence derived from genomic DNA, cDNA or RNA and optionally a second adapter, with primers comprising a 3' terminal first adapter hybridization sequence, wherein the first adapter hybridization sequence hybridizes to a region of the first adapter; (b) incubating the hybridized polynucleotide molecules formed in step (a) with a polymerase such that the polymerase extends 3' end of the primers to form primer extension products; and (c) incubating the primer extension products formed in step (b) with a 3' terminal transferase such that a random nucleic acid sequence is added to the 3' terminus of the primer extension products.

In some embodiments, a single stranded adapter is ligated to the 3' end of the random nucleic acid sequence following step (c).

In some embodiments, a double stranded adapter is ligated to the 3' end of the random nucleic acid sequence following step (c), wherein a portion of the adapter comprises a sequence complementary to the nucleic acid sequence on the primer extension product.

In some embodiments, the method further comprises amplifying the product of the ligation reaction.

In some embodiments, the method comprises: performing the method to label a library of polynucleotide molecules with unique variable sequences further comprising performing a sequencing process on the product of the amplification reaction.

A composition is provided. In some embodiments the composition comprises: (a) a mixture of primer extension products formed from a library of polynucleotide molecules comprising, in 3' to 5' order, a first adapter, a sequence derived from genomic DNA, cDNA or RNA, and a second adapter wherein the primer extension products comprise, in 5' to 3' order, a sequence complementary to the first adapter, a sequence complementary to the genomic DNA, cDNA or RNA derived sequence; and the sequence complementary to the second adapter; and (b) an excess amount of a synthetic oligonucleotides wherein the synthetic oligonucleotides comprise, in 3' to 5' order, a non-extendable 3' end, a sequence capable of hybridizing to the 3' terminal region of the primer extension products and a variable barcode sequence.

In some embodiments, the molar ratio of primer extension product to synthetic oligonucleotide is between 1:1 and $1:1 \times 10^{12}$.

In some embodiments, the composition further comprising a polymerase.

In some embodiments, the 5' end of the synthetic oligonucleotide is protected from exonuclease digestion.

In some embodiments, the second adapter comprises one or more deoxyuridines.

A composition comprising a mixture of primer extension products that are complementary to a single stranded polynucleotide library comprising an adapter on at least one end of a sequence derived from genome DNA or RNA; and a terminal transferase is also provided.

A kit is provided, comprising a polynucleotide molecule comprising a 5' adapter sequence and synthetic oligonucleotides comprising, in 3' to 5' order, a non-extendable 3' end, a sequence capable of hybridizing to the 3' terminal region a sequence complementary to the 5' adapter sequence and a variable barcode sequence.

In some embodiments, the kit further comprises a polynucleotide molecule comprising a 3' adapter sequence and a sample index primer comprising, in 5' to 3' order, a sample-specific barcode sequence and a sequence capable of hybridizing to at least a portion of the 3' adapter sequence.

In some embodiments, the kit further comprises a first primer capable of hybridizing to a sequence complementary to a sequence of the sample index primer located 5' of the sample-specific barcode sequence and a second primer capable of hybridizing to a sequence complementary to a sequence of the synthetic oligonucleotides located 5' of the variable barcode sequence.

EXAMPLES

While the examples provided herein describe specific temperatures, reagents, sequences, incubation times, buffers and other reaction conditions, such conditions exemplary and are not intended to be limiting. Similarly, the order of steps is described as an example and the order of steps may be modified and that certain steps may be added or deleted as expedient.

Example 1: Introduction of a UID into a DNA Library

Degenerate sequences were added to a DNA library using the methods generally illustrated in FIGS. 1A-1F and 2A-2G.

A second-strand synthesis reaction was performed on library molecules such that the newly formed primer extension product contained on the 5' end: the P7 sequence, the indexing sequence and the read 2 sequencing primer binding sequence; and on the 3' end: the read 1 sequencing primer binding sequence (FIGS. 3A-3C). Specifically, a library preparation of DNA fragments ligated to hairpin adapters at both ends were captured on streptavidin beads in 43 μL of water. A primer extension was performed by forming a reaction solution containing 41 μL of this DNA library preparation with 1 μL of 10 mM dNTPs, 5 μL of 10× ThermoPol® Reaction Buffer (New England Biolabs, Ipswich, Mass.), 2 μL of NEBNext® Multiplex Primer (New England Biolabs, Ipswich, Mass.) with 6 phosphorothioate bonds at the 5' end and 1 μL Q5 High-Fidelity DNA Polymerase, which was incubated at 72° C. for 10 minutes.

In some cases, the complex between the primer extension product and the DNA library template was denatured by incubation at 95° C. prior to addition of a UID template oligonucleotide, as depicted in FIG. 1A-1F. In other cases, the library template was digested from its 5' end by using Lambda exonuclease as depicted in FIG. 2A-2G. In such instances, the primer extension product was protected at the 5' end by phosphorothioate bonds whereas the 5' terminal phosphate on the original library molecules was not. To digest the 5' end of the library molecules, 1 μL of lambda exonuclease was added and incubated at 20° C. for 10 minutes. USER could be used in place of lambda exonuclease to similar effect.

A UID template was added to the 3' end of the primer extension product created in the second-strand synthesis reaction (FIG. 3E-3F). The 3' end of the primer extension product (specifically the read 1 sequencing primer binding sequence) was used as a defined region to hybridize with the 3' end of a UID template oligonucleotide, after which the 3' end of the primer extension product was further extended to incorporate a copy of the UID template sequence. Specifically, UID-template oligonucleotides containing a region complementary to the read 1 sequencing primer binding sequence, eight random nucleotides, and the P5 (Illumina sequence) were combined with a thermostable DNA polymerase, dNTPs and the primer extension product. This reaction was performed was performed in a 100 μL reaction mixture as follows that included 50 uL of primer extension reaction, 0.5 of μL Taq DNA Polymerase; 1 μL of 10 mM dNTPs, 2 μL of UID-template (0.05 μM), 5 μL 10× ThermoPol Reaction Buffer, and 41.50 μL of water. This reaction was cycled four times to ensure that a maximal number of molecules were barcoded The resulting barcoded primer extension product was combined with PCR primers that annealed to P5 and P7 primer recognition sequences such that only molecules with molecular IDs were amplified. The PCR reaction was run for 23 cycles using 2 μL of 100 μM PCR1 and PCR2 primers (FIG. 3G). The amplification product was purified using 0.9× Agencourt AmPure® (Beckman Coulter, Brea, Calif.) beads and eluted in a final volume of 20 μL, twice. The amplification products were then sequenced on the Illumina MiSeq platform.

When the process illustrated in FIG. 1 was performed, of the maximum 65,536 unique barcodes that can be generated with an 8 base random barcode, 64,381 were identified in the sequenced amplification product. When the process illustrated in FIG. 2 was performed, 56,551 unique barcodes were identified after sequencing.

Example 2: Introduction of a UID into a DNA Library Using a Terminal Transferase Degenerate sequences are added to a DNA library using the methods generally outlined in FIGS. 4A-4F and 5A-5E.

A library preparation of DNA fragments ligated to adapters at both ends is captured on streptavidin beads in 43 μL water. A primer extension is performed by combining 41 μL of the captured library molecules with 1 μL of 10 mM dNTPs, 5 μL of 10× ThermoPol Reaction Buffer and 2 μL of NEBNext Multiplex Primer, which is then incubated for 5 minutes at 95° C. followed by a ramp down to 30° C. at 0.1° C./second. On ice, 1 μL of Taq DNA Polymerase is added and the reaction solution is incubated at 72° C. for 5 minutes. The magnetic beads are immobilized using a magnet and the supernatant is transferred to a new tube to which 5 μL of terminal transferase is added. The terminal transferase reaction solution is incubated at 20° C. for 10 minutes, 75° C. for 10 minutes and then placed on ice. An adapter is added to the primer extension product by adding 20 μL of 5× Quick Ligation Buffer (New England Biolabs, Ipswich, Mass.), 10 μL of Quick T4 DNA Ligase (New England Biolabs, Ipswich, Mass.), 10 μL of dsDNA adapter with degenerate 3' end (0.05 μM) and 5 μL of $H_2O$ to the reaction solution. This solution is incubated overnight at 20° C. The resulting barcode labeled library is purified with 0.9× Agencourt AmPure beads and eluted in 23 μL. The purified labeled library is PCR amplified using 25 μL of LongAmp® Taq 2× Master Mix (New England Biolabs, Ipswich, Mass.) and 2 μL of 100 μM PCR1 & PCR2 primers. The resulting amplification product is purified using 0.9× Agencourt AmPure beads and eluted in a final volume of 20 μL.

Using the method described in FIGS. 4A-4F and 5A-5E, terminal transferase can add between 1 and 30 random nucleotides, theoretically generating up to $1\times10^{18}$ unique barcode sequences. In the method described in FIG. 4A-4F, the library is generated containing 6-10 random nucleotides, generating a theoretical maximum of between 4,096 and 1,048,576 unique sequences. The libraries are sequenced on the Illumina platform and analyzed by standard methods.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method, comprising:
(a) hybridizing a primer to a library of polynucleotide molecules comprising, in 3' to 5' order, a first adapter, a sequence derived from genomic DNA, cDNA or RNA, and a second adapter, wherein the primer hybridizes to the first adaptor;
(b) extending the 3' end of the hybridized primer to produce primer extension products;
(c) hybridizing the primer extension products with synthetic oligonucleotides, wherein:
(i) the synthetic oligonucleotides comprise, in 3' to 5' order, a non-extendable 3' end, a hybridization sequence, and a variable barcode sequence; and (ii) the hybridization sequence hybridizes to a 3' terminal region of the sequence complementary to the second adapter; and (d) incubating the hybridized primer extension products of step (b) with a polymerase such that the polymerase extends the 3' end of the primer extension products to form a further extended primer extension product.

2. The method according to claim 1, further comprising the step of denaturing the primer extension products from the polynucleotide molecules prior to step (c).

3. The method according to claim 1, wherein the 5' terminus of the primer is protected from exonuclease digestion and the method further comprises incubating the primer extension products and the polynucleotide molecules with a 5' exonuclease to remove a 5' terminal sequence from the polynucleotide molecules prior to step (c).

4. The method according to claim 3, wherein the second adaptor contains modified nucleotides that allow only partial digestion by a 5' exonuclease.

5. The method according to claim 4, wherein the modified nucleotides are internal phosphorothioate-containing nucleotides.

6. The method according to claim 4, wherein the 5' exonuclease removes 10-20 bases from an end of the second adaptor leaving a single strand overhang.

7. The method according to claim 1, further comprising removing a 5' terminal sequence from the polynucleotide molecules after step (b) and prior to step (c), leaving a 3' overhang.

8. The method according to claim 1, further comprising amplifying the further extended primer extension products produced in step (d).

9. The method of claim 1, wherein extension of the primer extension products in step (d) adds the complement of the variable barcode sequence onto the primer extension products.

* * * * *